(12) United States Patent
Fisher (10) Patent No.: US 6,955,660 B2
(45) Date of Patent: Oct. 18, 2005

(54) INTERNAL EXPANSION SYRINGE ADAPTOR

(76) Inventor: Michael Alan Fisher, 1609 Winslow Dr., Blacksburg, VA (US) 24060

( * ) Notice: Subject to any disclaimer, the term of this patent is extended or adjusted under 35 U.S.C. 154(b) by 165 days.

(21) Appl. No.: 10/237,020

(22) Filed: Sep. 9, 2002

(65) Prior Publication Data

US 2004/0049162 A1 Mar. 11, 2004

(51) Int. Cl.$^7$ .......................... A61M 5/00; A61M 25/16; A61M 25/18; A61M 39/00; A61M 39/10
(52) U.S. Cl. ....................................... 604/240; 604/533
(58) Field of Search ................................ 604/240, 241, 604/243, 533, 534, 535, 536, 187

(56) References Cited

U.S. PATENT DOCUMENTS

| | | | | |
|---|---|---|---|---|
| 3,402,713 A | * | 9/1968 | Senkowski et al. | 604/241 |
| 4,187,848 A | * | 2/1980 | Taylor | 604/243 |
| 5,002,538 A | * | 3/1991 | Johnson | 604/240 |
| 5,464,400 A | * | 11/1995 | Collins | 604/538 |
| 5,489,205 A | * | 2/1996 | Davis et al. | 433/80 |
| 5,759,178 A | * | 6/1998 | Wells | 604/240 |
| 5,919,169 A | * | 7/1999 | Grams et al. | 604/241 |
| 6,112,743 A | * | 9/2000 | Denton | 128/200.14 |

* cited by examiner

Primary Examiner—Nicholas D. Lucchesi
Assistant Examiner—Catherine S. Williams
(74) Attorney, Agent, or Firm—Chalin A. Smith; Smith Patent Consulting

(57) ABSTRACT

An adaptor for connecting a syringe to an aspiration and/or irrigation device, typically a medical device such as a catheter, cannula or needle, is described herein. The adaptor is comprised of two components: a deformable elastomeric expansion sleeve and a relatively rigid insertion body. The expansion sleeve is essentially an elastomeric plug that forms a tight seal about the inner and outer surfaces of the syringe tip when deformed by the relatively rigid insertion body. The adaptor assembly described herein allows for full visualization of the syringe contents when in use and is compatible with multiple syringe components. The adaptor assembly is also relatively easy to manufacture and maintain. It provides a fluid-seal that adequately tolerates the mechanical loads such as torsion, mechanical moment, shear, and longitudinal loads expected during normal use.

28 Claims, 11 Drawing Sheets fig. 1A fig. 1B fig. 1C fig. 1D fig. 3A fig. 3B fig. 4A fig. 4B fig. 4C fig. 5 fig. 8 fig. 9a fig. 9b fig. 13

INTERNAL EXPANSION SYRINGE ADAPTOR

FIELD OF THE INVENTION

The invention relates to an adaptor for connecting a syringe to an aspiration and/or irrigation device, typically a medical device such as a catheter, cannula or needle. More particularly, the invention relates to a two component syringe adaptor composed of an elastomeric expansion sleeve and a more rigid insertion body.

BACKGROUND OF THE INVENTION

Syringes are used in various industries, including manufacturing, medicine, and biology, for dispensing and aspirating fluid materials. A syringe is essentially a hollow barrel with an open end serving as the entrance for a plunger or piston and a terminal end containing a shoulder with a specialized tip used to dispense the substance contained within the syringe barrel or aspirate fluid materials into said barrel. Because of the numerous uses for syringes, there are a myriad of tip designs and each tip is specialized for a particular application. The basic syringe tip consists of a frustoconical nose that is elongated and/or shaped for the intended use.

A syringe is often fitted with a detachably retained aspiration or irrigation device configured to perform the intended task. Examples of such devices include suction tubes, irrigation hoses, dispensing nozzles, catheters, cannulas and needles. A specialized connector or adaptor is often required to attach the various devices to the number of syringe tips. Several designs for adaptors have been popularized, a number of which are discussed herein.

The Luer slip is the most widely used syringe adaptor design. The male Luer tip of the syringe is a small diameter frustoconical shape with a small lumenal opening communicating with the inside of the syringe. The female Luer slip adaptor is a frustoconical tip of substantially the same dimensions as the male Luer tip. A female Luer slip is fitted at one end of an irrigation and/or aspiration device to allow the device to be attached to the syringe in such a way as to allow fluid communication between the device and the syringe. The female Luer slip is inserted over the male Luer tip of the syringe to form a combination device. As the parts are pressed together, the female Luer slip is deformed azimuthally and radially. The elasticity of the female Luer material compresses the male Luer tip, forming a friction fit and an effective fluid seal. The Luer slip adaptor is simple and efficient; however, it allows for motion and loosening between the syringe and the device. Torsional, longitudinal, and moment loading of the Luer slip adaptor results in separation of the adaptor from the syringe. Also, the maximum diameter of fluid communications between the syringe and the adaptor is limited to a channel of approximately 1 millimeter in diameter. Due to these drawbacks, other syringe tip designs have been popularized.

A Luer-Lok type syringe adaptor is described by Senkowski et al., in U.S. Pat. No. 3,402,713, incorporated by reference herein. The Luer-Lok is perhaps the second most widely used syringe adaptor design. The Luer-Lok adaptor allows a device to be attached to the tip of a syringe using the Luer slip design in combination with a screw mechanism. The Luer-Lok system includes a coaxial internally threaded barrel disposed about the periphery of the male Luer tip on the syringe and two flanges located at the lumenal end of the female Luer slip of the connecting device. The threads of the syringe's Luer tip accommodate the flanges of the female Luer slip. Rotating the female Luer slip with respect to the syringe mates the two devices. Because the threads and flange hold the Luer slip onto the male Luer tip in a rigid manner, there is less motion and instability between the syringe and the attached device than with the previous by described Luer slip adaptor.

The Luer-Lok adaptor mechanism forms a rigid combination device with a fluid-tight seal. Despite the improvement over the Luer slip adaptor, the Luer-Lok adaptor shares the drawback of allowing only a small-diameter communication between the syringe and the attached device. Moreover, torsional loads will still cause rotation and separation of the adaptor from the syringe. Likewise, sufficient longitudinal and mechanical moment loading will cause the Luer-Lok to pull out of the threaded barrel, thereby separating the devices.

The Luer slip adaptor is relatively weak and routinely fails to maintain a seal during many applications due to mechanical moments, torque, high pressures, or significant temperature changes from room temperature. Also, the Luer design restricts the maximum diameter of fluid communication with the syringe barrel to less than 1 mm. This restricted diameter increases resistance to flow to the fourth power in the reduction of the diameter (Hagen-Poiseuille flow). The small diameter restriction also makes the communication of fluid slurry with semi-solid aggregates with diameters greater than 1.0 mm or a high-density of semi-solids virtually impossible. Finally, an improperly seated Luer will leak fluid and is hazardous to the user due to biocontamination in a medical environment.

Another adaptor is described by Johnson et al, in U.S. Pat. No. 5,002,538, incorporated by reference herein. The Johnson adaptor is designed to duplicate the contours of the syringe tip, shoulder, and barrel. When the Johnson adaptor is inserted over the syringe, the adaptor forms a friction fit with the syringe's tip and barrel. One benefit to Johnson's design is the dual friction fits at the syringe tip and barrel, which create two fluid-tight seals that retard leakage from the assembly. The external friction fit is also an improved mechanism to resist the mechanical moments, axial torques, and longitudinal and shear loading applied during use.

A drawback to the Johnson adaptor is the propensity to lose the friction fit about the syringe barrel, thereby causing fluid leaks, separation of the devices, or creation of a projectile of the adaptor when pressure is applied from within the syringe. Another drawback is the potential for a mechanical misfit between the syringe and the adaptor (e.g., the syringe barrel is too large to fit into the collar of the adaptor or the adaptor is too large to form a friction fit with the syringe), thus rendering the adaptor ineffective. Yet another drawback is the inability to visualize material within the syringe because the adaptor mechanism covers the syringe tip and barrel.

The Johnson adaptor must be manufactured using severe dimensional tolerances; thus its design is ill adapted for mass production. Moreover, when a pressure is applied from within the syringe, the Johnson adaptor is prone to detachment from the syringe barrel and become a projectile. Also, because most syringes are manufactured from plastic and are not entirely uniform in dimension, the Johnson adaptor tends to fit some syringes well while other syringes from the same manufacturer (and even the same production lot) will be too loose or too tight to use. Also, surface debris or liquids can prevent this adaptor from creating a reliable fluid seal. Finally, this adaptor covers one end of the syringe barrel and tip such that visualization the syringe contents is restricted.

Another adaptor design is described by Wells et al., in U.S. Pat. No. 5,759,178, incorporated by reference herein. The Wells adaptor forms an internal and/or external threaded fit and/or groove-fit with the syringe tip. This adaptor claims to use the syringe's shoulder to support "a large amount of torque". In one embodiment, the Wells device has an external thread that is used to groove the outside of the syringe's tip. In another embodiment, the device has an internal thread for an inside/outside connection.

A drawback to the Wells adaptor is the manufacturing problem of forming inside and outside grooving mechanisms and/or screw threads in close proximity. Another drawback is the inability to adequately clean internal threads on medical devices, leading to an unsterile device. Yet another drawback to the Wells adaptor is the fact that the syringe has been permanently grooved, deformed, or otherwise damaged by the adaptor fixation mechanism (cutting threads or grooving mechanism). Another drawback to the Wells adaptor is that an air pocket can develop between the threads of the adaptor and the material of the syringe tip. This air pocket inside the lumen of the syringe tip can reduce the level of suction or induce total loss of suction during use. Another problem with the Wells adaptor is that it does not allow visualization of the contents of the syringe within the syringe tip.

Despite suggestions to the contrary, the Wells adaptor is subject to detach when a torque-load is applied. Also, the adaptor is difficult to clean and maintain because of its internal and/or external grooving mechanisms. Maintenance issues are critical in the medical industry because unclean instruments are unsterile and can cause or spread infection. Finally, because this adaptor attaches to the syringe tip, it, too, obscures the last couple of milliliters of syringe contents.

Another adaptor is described by Grams, et al., in U.S. Pat. No. 5,919,169, incorporated by reference herein. The Grams' adaptor consists of two pieces: a plug with a proximal internal frustoconical receptacle to receive a syringe tip, a distal threaded receptacle to receive a cannula nose, and a cannula nose having a proximal end that inserts into the distal collar and the lumen of the syringe tip. The plug and cannula nose have mating threads so that once the two are screwed together, the nose presses into the syringe tip and forms a gas-tight and liquid-tight seal. The Grams adaptor forms a friction/compression fit with the syringe's tip.

Significant drawbacks to the Grams adaptor are found in the mechanisms used to fix the plug to the syringe; specifically, an unreliable friction fit or an inconvenient adhesive or "welding" seating and sealing mechanism. If an adhesive or welding technique is used, the syringe becomes permanently changed and cannot be used with other devices. Moreover, in a surgical environment, the Grams adaptor is likely to fall off the syringe due to inadequate friction. An inadequate friction fit can also result in a loss of continuity between the nose and plug or the plug and the syringe or the nose and the syringe. Finally, the Grams adaptor like others described above, also impairs visualization of material within the syringe tip.

The Grams adaptor requires an awkward mounting procedure. Specifically, one must fix the plug to the syringe tip using "welding or other mounting methods", insert the nose into the syringe tip, and screw the plug/syringe/nose assembly until the threads are mated and the adaptor pinches the syringe tip between the nose and the plug. Also, the Grams adaptor significantly adds to the length of the assembly, thus forming an awkward combination device. Furthermore, the gas and liquid pinch seal can be broken when either a mechanical moment or a torsional load is applied. Both types of loading occur repeatedly in many procedures. The Grams adaptor is also difficult to clean and maintain because of its screw threads. This raises concerns about maintenance, sterility, and product safety. Finally, the Grams adaptor obscures the last couple of milliliters of syringe contents due to its mounting on the syringe tip.

Other adaptor assemblies for connecting syringes to needles, catheters, atomizer nozzles and the like are described in U.S. Pat. No. 3,366,286 (Kloehn), U.S. Pat. No. 4,187,848 (Taylor), and U.S. Pat. No. 6,112,743 (Denton), incorporated by reference herein.

A common problem to all these designs is that each adaptor is particularly configured to fit only one type of syringe, from a particular manufacturer, and thus is incapable of fitting any other brand or size of syringe unless it is specifically redesigned to do so.

As noted, each of these syringe adaptors has significant problems.

None of these adaptors provide for full visualization of the syringe contents or can be applied to more than one type of syringe. Several adaptors are difficult to clean and the fluid-seal for each design is often compromised during normal use. Moreover, none of the related art contains a design that adequately tolerates the mechanical loading expected during use, including torsion, mechanical moment, shear, and longitudinal loads.

SUMMARY OF INVENTION

Accordingly, it is an object of the invention to provide a syringe adaptor assembly that provides a secure, fluid tight connection, allows for full visualization of the syringe contents, is easy to manufacture and maintain, and is compatibile with multiple syringe embodiments.

A further object of the present invention is to provide a syringe adaptor assembly that forms two continuous seals so as to ensure that the fluid communication between the adaptor and the syringe is uninterrupted and uncompromised during use of the assembly.

Another object of the present invention is to provide a deformable expansion sleeve that accommodates for dimensional variability of both the syringe tip and the insertion body, and is insensitive to dimensional instability associated with mass production for any component of the assembly (e.g., syringe, expansion sleeve, or insertion body) accommodates for dimensional variability between manufacturers of syringes.

Another object of the present invention is to provide a syringe adaptor that allows for full visualization of the syringe contents and in which there is no likelihood for an air pocket to form.

Another object of the present invention is to provide a syringe adaptor that can withstand various forms of mechanical loading and thermal changes without interrupting or corrupting the fluids passing through the adaptor mechanism.

Another object of the present invention is to provide a syringe adaptor that can withstand torsional loading and rotation of the adaptor without resulting in detachment of the device or compromise of the fluid-seal. Moreover, mechanical moments, longitudinal loading, and shear loading should not remove the adaptor from the tip of the syringe or interrupt the fluid seal.

Another object of the present invention is to provide a syringe adaptor whose components can be easily separated and cleaned to ensure future sterility of the assembly. The surfaces of the adaptor of the present invention are preferably smooth and free of the invaginations and convolutions that harbor most infectious agents.

Another object of the present invention is to provide a syringe adaptor that does not alter, damage, or deform the syringe tip, leaving it in pristine condition and without adhesive or welding spots.

Another object of the present invention is to provide a syringe adaptor having reversible locking and sealing mechanisms, wherein the adaptor can be applied multiple times to multiple syringes during the same procedure without any loss of function to the syringe or adaptor mechanism.

Thus, in response to these objects and needs, the syringe adaptor of the present invention is composed of two parts: an expansion sleeve and an insertion body. The expansion sleeve is essentially an elastomeric plug that, when deformed by the relatively more rigid insertion body, forms a tight seal about the inner and outer surfaces of the syringe tip.

In a preferred embodiment, the expansion sleeve comprises a hollow nose connected to a conical collar coaxially disposed about the periphery thereof by an annular shoulder. The hollow nose is sized to have an outside diameter that can be inserted into the lumen of the syringe tip and an inside diameter that is smaller than the shaft of the insertion body. The conical collar is sized to accommodate the exterior of the syringe tip and lockingly engage the insertion body when the two are pressed together. The nose, collar and shoulder are preferably configured such that when the nose is fully inserted into the syringe tip, the collar is snug against the end of the syringe tip.

In a preferred embodiment, the insertion body comprises an insertion shaft connected to a locking barrel coaxially disposed about the periphery thereof by an annular shoulder or hub. The insertion shaft is sized to have an outside diameter smaller than the lumen of the syringe tip but larger than the lumen of the hollow nose of the expansion sleeve. The locking barrel is sized to have an inside diameter substantially similar to the outside diameter of the conical collar of the expansion sleeve and an outside diameter sufficiently large to provide adequate mechanical strength to grip the conical collar when inserted over said collar as the devices are pressed together. The shaft, barrel and shoulder are preferably configured such that when the insertion body is fully inserted into and over the elastic adaptor, the shoulder of the insertion body is snug against the shoulder of the elastic adaptor.

The outside surface of the conical collar and the inside surface of the locking barrel are preferably fitted with engaging locking elements that maintain the expansion sleeve and the insertion body in a secure locking relationship. For example, the collar and barrel may be fitted with coordinating screw threads or engaging flanges, projecting in opposite directions.

The adaptor of the present invention provides for a mechanically secure and fluid tight connection between syringe and attached device. In a particular embodiment, the expansion sleeve and insertion body are configured such that the insertion of the shaft of the insertion body into the hollow nose of the expansion sleeve causes the nose to radially and circumferentially deform. This action causes the syringe tip to be lockingly engaged between the deformed hollow nose and the coaxially disposed conical collar, forming a lock-and-key seal with the inside dimensions of the syringe tip. As the insert body is inserted over the expansion sleeve, the coordinating locking elements disposed on the conical collar and locking barrel will engage, thereby preventing the insertion body from loosening from the expansion sleeve/syringe assembly.

The adaptor of the present invention is particularly useful for connecting a syringe to an aspiration or irrigation device, typically a medical device such as a catheter, cannula or needle. Although the invention is particularly suited to medical applications, such as liposuction, it is clearly not limited to the medical realm. Many syringes are used in industrial applications, for example to dispense adhesives and the like. Conventional Luer syringes are inadequate for many applications, such as those that involve large particles or require large fluid bore. Likewise, the remaining existing art is also inadequate, due to the inability to withstand high pressure, turbulent flow, or intense torque or due to obstruction of visualization of the syringe contents. As noted, the adaptor of the present invention overcomes these issues. Moreover, the internal expansion adaptor eliminates the air-pocket left by Luer devices and it would unplug the syringe tip when removed.

These and other objects of the invention will be evident from the following description, taken together with the attached drawings and appended claims.

BRIEF DESCRIPTION OF DRAWINGS

Referring now to the drawings, which illustrate particular embodiments of the present invention and wherein like reference numerals refer to like parts in different views or embodiments.

DETAILED DESCRIPTION OF THE PREFERRED EMBODIMENTS OF THE INVENTION

In the context of the present invention, the following definitions apply:

The term "distal" refers to that end or portion which is situated farthest from the hand of the operator and closest to the body of the patient when the device is in use.

The term "proximal" refers to that end or portion situated closest to the hand of the operator and farthest away from the body of the patient when the device is in use.

For reasons of clarity, the present invention is described in this disclosure in terms of use with hand-actuated syringes as are commonly utilized in medical, dental, and veterinary applications, and the use of the invention is related generally in terms of medical applications. However, syringes which apply force by hydraulic, pneumatic and other means may also be used with the present invention. Moreover, as should be readily apparent to persons of ordinary skill in the art, the present invention may be used with a large variety of syringe-like dispensing or aspirating devices, in a number of applications, including manufacturing, engineering and industrial purposes, and is not restricted to medical applications.

Thus, in the context of the present invention, the term "syringe" encompasses any device wherein pressure-actuated dispensation or aspiration of fluid materials is carried out. Syringes suitable for use with the adaptor of the present invention generally comprise an open-ended hollow barrel having an actuable piston or plunger disposed therein for generating the requisite force or pressure. In a preferred embodiment, the syringe barrel has a tapered, generally frustoconical, tip that is specially elongated or shaped for the intended use.

The term "fluid material" as used herein refers generally to all types of liquids including, but not limited to, pharmaceutical solutions and biological fluids (such as blood or plasma), pastes (such as, caulks or adhesives), gels, slurries (such as, cellular and tissue extractions) and other like materials which may be aspirated, dispensed, or extruded through a nozzle or applicator by application of pressure.

The adaptor of the present invention is not limited to any particular application or syringe design. Syringes of widely varying size, shape, or material may be used in conjunction with the inventive adaptor.

In a preferred embodiment, the syringe comprises a hand-actuated, large lumened barrel having a specialized tip, such as a toomey tip, a catheter tip, a male Luer tip, or the like. The toomey tip is short and rather wide, whereas the catheter tip is elongated and terminates with a relatively small opening, and the male Luer tip is short and small in diameter. These tips may be curved to facilitate angled material aspirating/dispensing and some tips are eccentric with respect to the syringe barrel. In another embodiment, the syringe is a liposuction handle.

As noted above, the adaptor of the present invention is comprised of two components: an expansion sleeve and an insertion body. The expansion sleeve functions as a sealing mechanism, providing a secure fluid connection, of a strength sufficient to tolerate torsional and mechanical loads, without obstructing the visualization of the syringe contents. An illustrative embodiment of the expansion sleeve is shown in FIGS. 1A–1D. Alternate embodiments of the expansion sleeve are shown in FIGS. 9A–B and 11A–B. In the figures, like elements are designated with like reference numerals. The following elements are common to the three embodiments of syringe adaptor depicted herein:

an expansion sleeve (100) having proximal (102) and distal (101) ends and a central sleeve lumen (106), comprised of (i) a sleeve nose (103) having inner (105) and outer (104) surfaces, (ii) a sleeve collar (110) having inner (112) and outer (111) surfaces, and (iii) an annular surface (107) connecting sleeve nose to collar; and an insertion body (200) having proximal (201) and distal (202) ends and a central body lumen (206), comprised of a body shaft (203) having an outer surface (204) that acts to compress the sleeve nose inner surface (105) against the inner surface (303) of a syringe tip (301).

The figures further depict the syringe adaptor in conjunction with a conventional syringe. Again, like elements of the syringe are designated with like reference numerals. Specifically, syringe (300) is depicted as having a frusto-conical syringe tip (301) with outer (302) and inner (303) surfaces and a central tip lumen (306), a syringe barrel (305), and a syringe shoulder (305) connecting syringe tip to barrel.

Figure 1A:
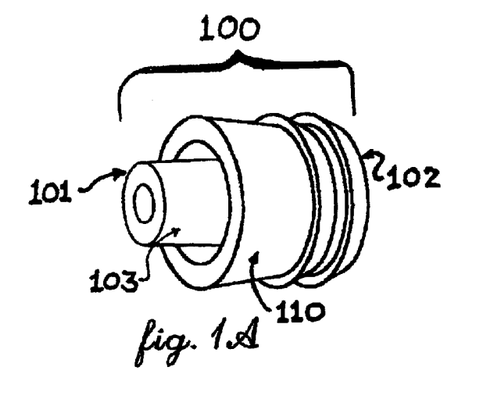
FIG. 1A is an enlarged isometric view of the expansion sleeve.
Figure 1B:
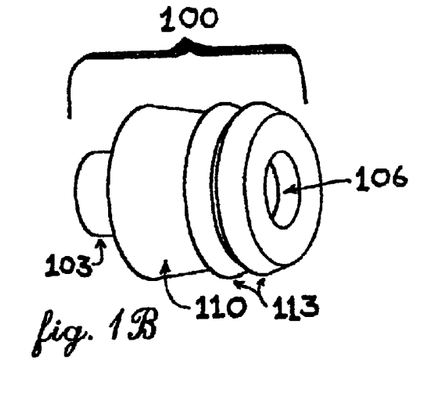
FIG. 1B is an enlarged isometric view of the expansion sleeve of FIG. 1A from a perspective angle.
Figure 1C:
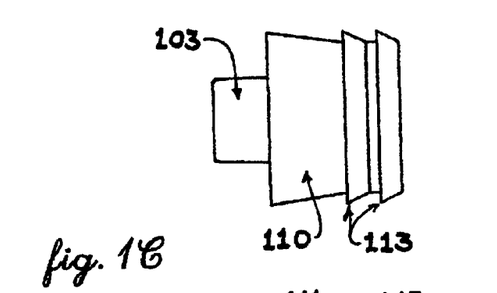
FIG. 1C is an enlarged side view of the expansion sleeve of FIG. 1A.
Figure 1D:
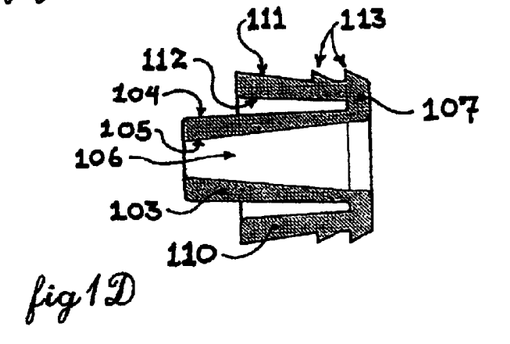
FIG. 1D is an enlarged side cross-sectional view of the expansion sleeve of FIG. 1A.

When the syringe adaptor of the present invention is engaged with a conventional syringe, the central lumen of the syringe tip, expansion sleeve and insertion body are concentrically disposed about each other so as to allow for uninterrupted and uncompromised fluid communication between syringe barrel (305) and an irrigation or aspiration device (not shown). With specific reference to FIGS. 1A–1D, the expansion sleeve (100) is composed of a central frustoconical hollow nose (103) and a conical collar (110) coaxially disposed about the nose. The expansion sleeve (100) has central lumen (106) running from proximal end (101) to distal end (102), along the length of the nose (103). As shown in FIG. 1D, the nose (103) and conical collar (110) are joined at the distal end (102) of sleeve (100) by an annular shoulder (107).

The nose (103) and collar (110) are configured to receive a conventional frustoconical syringe tip (not shown) in the space between outer surface (104) of nose (103) and an inner surface (112) of collar (110). Particularly, the nose (103) fits within the interior of the syringe tip and the conical collar (110) accommodates the exterior of the syringe tip. When in use in combination with the insertion body (see FIGS. 3A–B and 4A–C), the two sleeve components coordinate to lockingly engage the syringe tip.

In a preferred embodiment, the outer surface (111) of the collar (110) is fitted with one of more locking elements that coordinate with mating locking elements disposed on the insertion body itself (not shown) or a component that coordinates with the insertion body. As shown in FIG. 1C, the locking elements may comprise one or more projecting flanges (113). Alternatively, the locking mechanism may comprise a coordinating ratchet and pawl, screw thread and screw track, notch and groove, notch and keyway, lock and key, lever and catch, cam and cam follower, spline and gear or the like. While the particular locking mechanism used is not critical to the present invention, the locking mechanism should be sufficiently strong to provide a secure connection to withstand torsional and mechanical loads that may be applied in use. Furthermore, the locking mechanism should be of a type that is relatively simple to manufacture, such as by injection molding.

To perform the intended function, the expansion sleeve (200) must deform easily yet at the same time maintain a deformed state when exposed to thermal changes and mechanical loads. The expansion sleeve (200) is preferably formed from a material that is sufficiently elastic and flexible yet incompressible (e.g., no change in volume in response to changes in pressure). Such materials are conventional in the art. Preferred materials include, but are not limited to, cross-linked silicones, low density polyethylene, rubbers, waxes, fabrics, textiles, felts, weaves, low-modulus metals, hydrogels, swelling materials (anhydrous or non-water-absorbing), clays, bingham plastics, caulks, glues, potting materials and the like.

The insertion body of the adaptor of the present invention acts as a press, deforming the nose (103) of the expansion sleeve to fit snugly within the syringe tip lumen (not shown), and a lock, preferably coordinating with the locking element (s) disposed on the sleeve's collar (110) to retain the assembly (e.g., syringe, sleeve and insertion body) in a locked configuration. An embodiment of the insertion body of the inventive syringe adaptor, is shown in FIGS. 2A–2D.

Figure 2A:
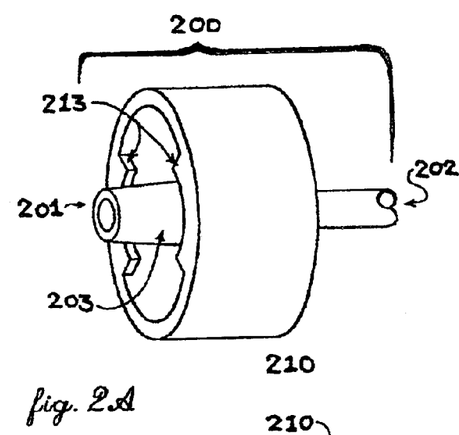
FIG. 2A is an enlarged isometric view of one embodiment of the insertion body.
Figure 2B:
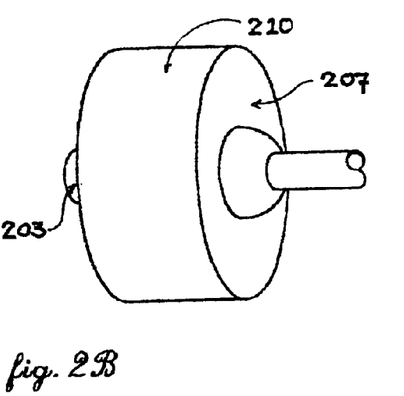
FIG. 2B is similar to FIG. 2A except for a change in the perspective angle for the isometric view.

As shown in FIG. 2A, the insertion body (200) has a proximal end (201), that receives the expansion sleeve (not shown), and a distal end (202), to which an aspiration or irrigation device (not shown), such as a cannula, needle, catheter, tube or the like, is attached. The insertion body (200) comprises a hollow, tubular shaft (203) connected to a locking barrel (210) coaxially disposed about the periphery thereof by an annular shoulder (207). The insertion body (200) further has central lumen (206) running there through, along an axis of the shaft (203).

Figures 2C, 2D:
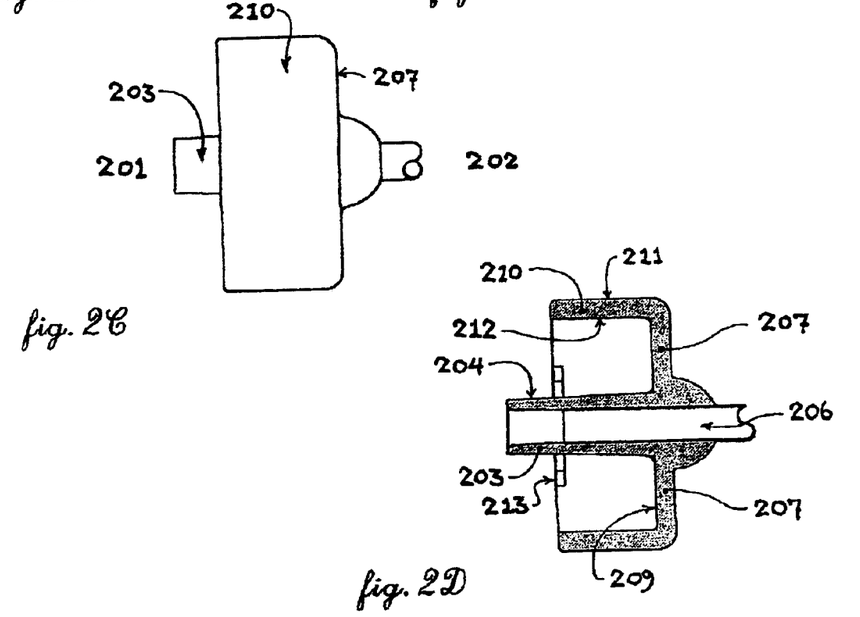
FIG. 2C is an enlarged side view of the insertion body of FIG. 2A.
FIG. 2D is an enlarged side cross-sectional view of the insertion body of FIG. 2A.
Figure 3A:
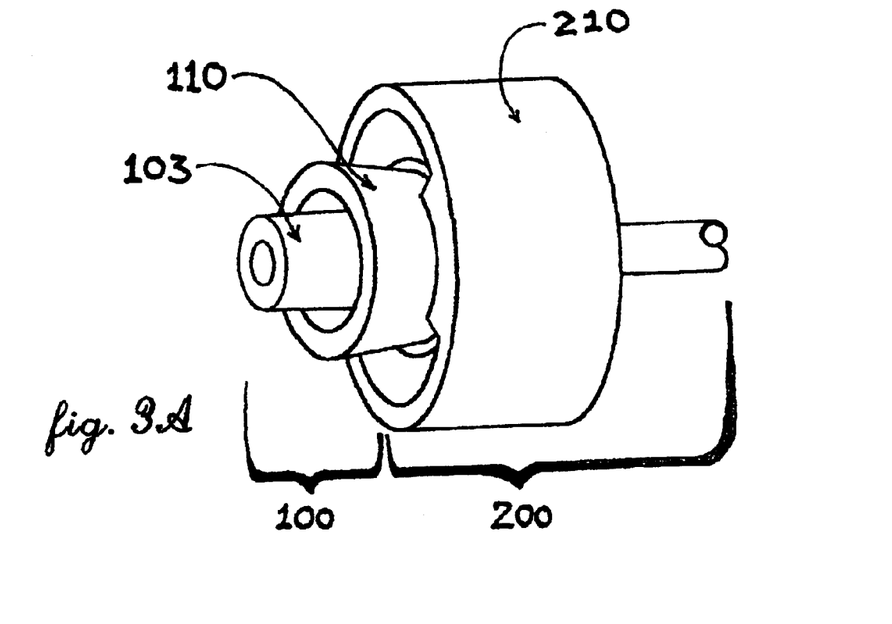
FIG. 3A is an enlarged isometric view of the assembly of the expansion sleeve of FIG. 1A and the insertion body of FIG. 2A.
Figure 3B:
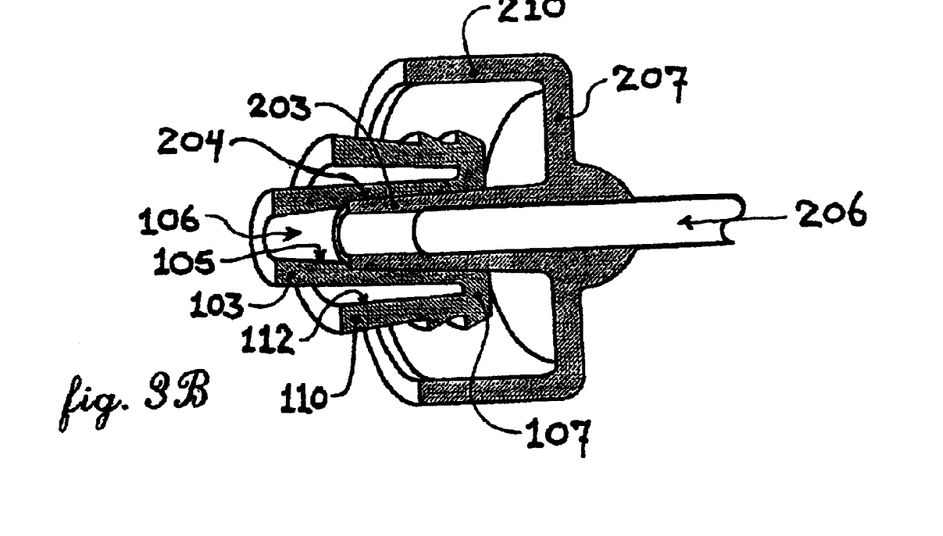
FIG. 3B is an enlarged isometric cross-sectional view of the assembly of the expansion sleeve of FIG. 1A and the insertion body of FIG. 2A.
Figure 4A:
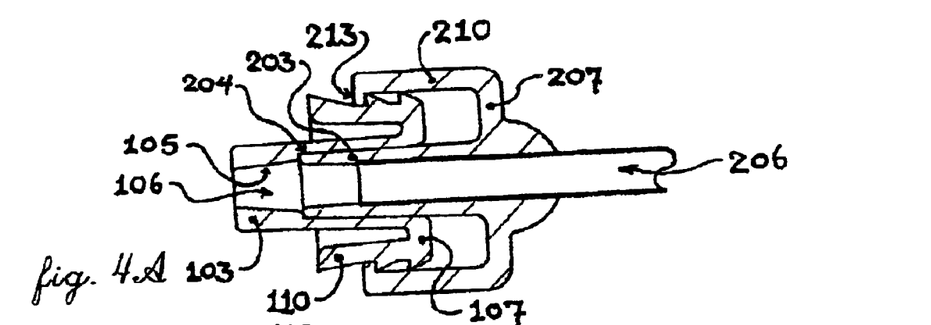
FIG. 4A is an enlarged cross-sectional side view of the assembly of the expansion sleeve of FIG. 1A and the insertion body of FIG. 2A.
Figure 4B:
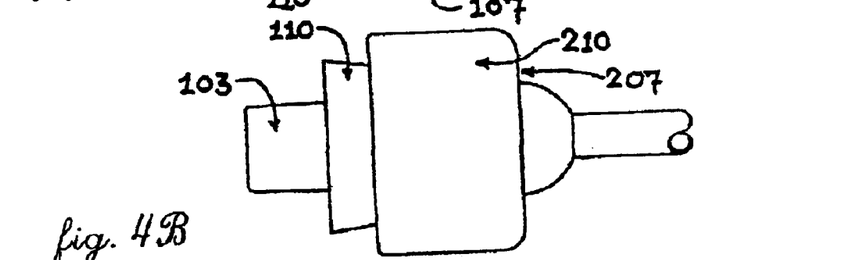
FIG. 4B is an enlarged side view of the assembly of the expansion sleeve of FIG. 1A and the insertion body of FIG. 2A.
Figure 4C:
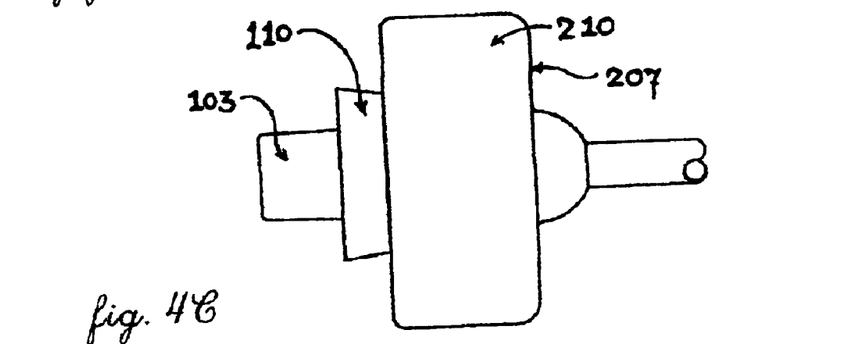
FIG. 4C is to a top view of the expansion sleeve/insertion body assembly of FIG. 4A.

As shown in FIG. 2D, the shaft (203) and locking barrel (210) are configured to receive the expansion sleeve (not shown) in the space between the shaft outer surface (204) and the barrel inner surface (212). When in use in combination with the expansion sleeve, the sleeve shoulder engages and abuts the inner surface (209) of the insertion body shoulder (207). The outer diameter of the insertion body shaft (203) should be greater than the inner diameter of the expansion sleeve nose (103) but substantially equivalent to the inner diameter of the syringe tip. This allows the insertion body shaft (203) to deform the expansion sleeve nose (103) to seal against the interior of the syringe tip.

As noted above, the barrel inner surface (212) is preferably fitted with one of more locking elements that coordinate with mating locking elements disposed on the sleeve collar. In the embodiment shown in FIG. 2A, the locking elements comprise one or more projecting flanges (213). However, the particular locking mechanism utilized is not critical to the present invention. The barrel outer surface (211) may optionally be configured with one or more finger recesses (not shown) to assist in manipulation. The outer surface may further contain indicia denoting the orientation of the attached device (e.g., a marker that correspond to catheter "top side" or "suction port").

To perform as intended, the insertion body should be more rigid than the expansion sleeve. Exemplary preferred materials useful for the manufacture of the insertion body include, but are not limited to, metal, engineering plastics, ceramics, and the like.

As shown in FIGS. 3A–B and 4A–4C, the shaft (203), barrel (210) and shoulder (207) of the insertion body (200) are preferably configured such that the expansion sleeve (100) fits snugly the within the annular recess of insertion body, formed between shaft outer surface (204) and barrel inner surface (212). The shaft outer surface (204) is designed to engage the nose inner surface (105), to flex the nose (103) radially so that the syringe lumen (not shown) is engaged between the nose outer surface (105) and collar inner surface (112).

Figure 5:
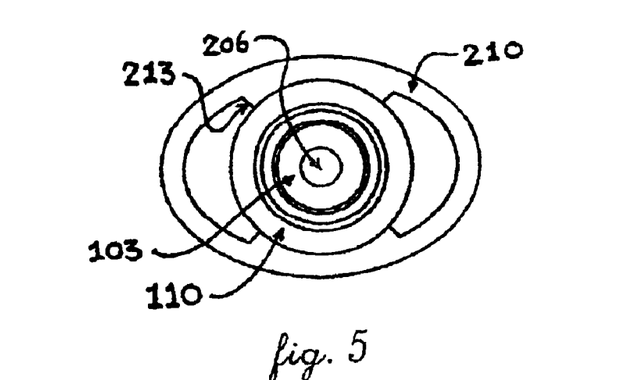
FIG. 5 is an enlarged end view of the expansion sleeve/insertion body assembly of FIG. 4A.

To perform as intended, the outside diameter of the insertion shaft should be larger than the lumen diameter of the expansion sleeve nose but substantially equivalent to syringe tip lumen diameter. Likewise, the locking barrel is sized to have an inside diameter substantially similar to the outside diameter of the conical collar of the expansion sleeve and an outside diameter sufficiently large to provide adequate mechanical strength to grip the conical collar when inserted over the collar as the devices are pressed together. The end view of the adaptor assembly, depicting the coordination of these components, is shown in FIG. 5.

As noted above, the inventive adaptor may be used in combination with any number of syringe-like dispensing means. An embodiment of the syringe adaptor of FIG. 1A in combination with a conventional toomey tip syringe is shown in FIGS. 6A–B, 7A–B, and 8.

Figure 6A:
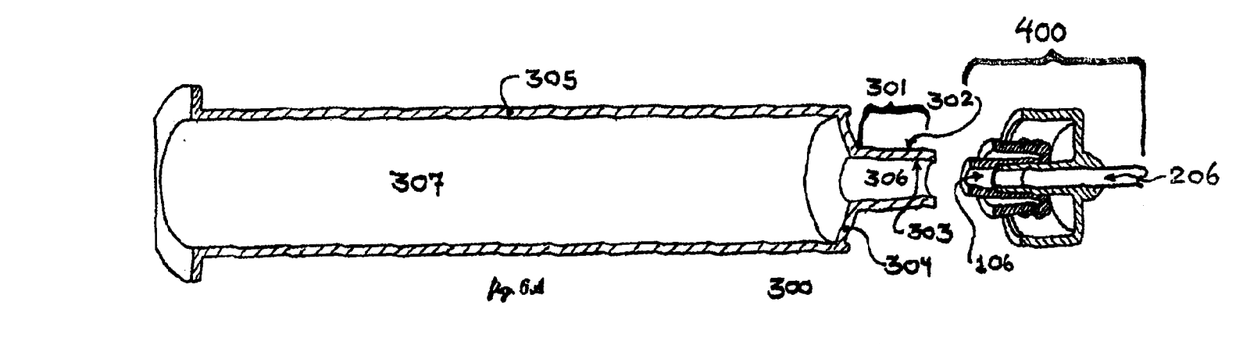
FIG. 6A is an isometric cross-sectional view of the syringe and the expansion sleeve/insertion body assembly of FIG. 4A.
Figure 6B:
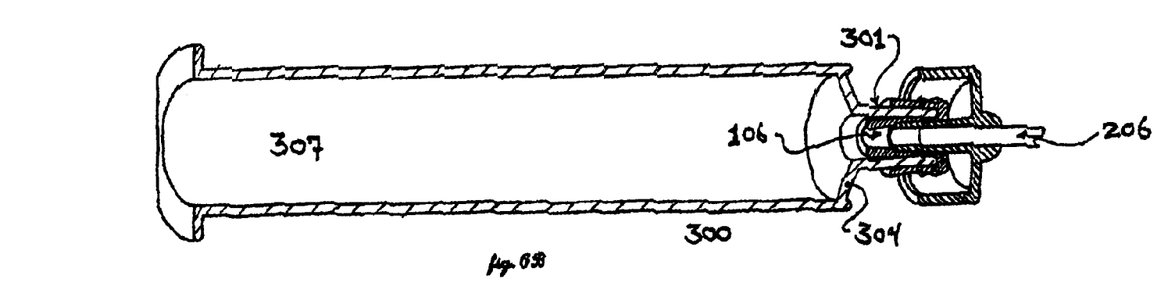
FIG. 6B is the expansion sleeve/insertion body assembly as shown in FIG. 6A inserted into the lumen of the syringe tip.

FIG. 6A depicts the syringe (300) and adaptor (400), comprised of expansion sleeve (100) together with insertion body (200), prior to attachment. FIG. 6B depicts the syringe (300) with adaptor (400) secured thereon. When attached in combination, syringe tip lumen (306), sleeve lumen (106) and insertion body lumen (206) form a fluidically sealed passageway for transporting liquid materials to or from the syringe barrel interior (307).

Figure 7A:
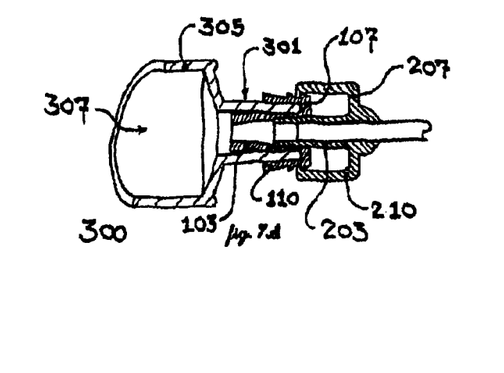
FIG. 7A is a side cross-sectional view of the expansion sleeve/insertion body assembly as in FIG. 4A as inserted into the lumen of the syringe with a cropped syringe body.
Figure 7B:
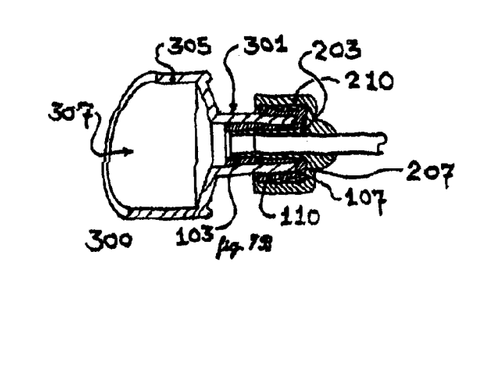
FIG. 7B is the expansion sleeve/insertion body assembly as in FIG. 7A fully inserted into the lumen of the syringe tip wherein the locking barrel is engaged.

The components of the syringe-adaptor assembly preferably coordinate as shown in FIGS. 7A and 7B. Specifically, as the insertion body (200) is inserted into the expansion sleeve (100), the insertion shaft (203) deforms the nose (103) radially and circumferentially. The deformed hollow nose (103) forms a tight fit between syringe tip inner surface (303) and the shaft outer surface (204). When deformed, the nose (103) has a frustoconical shape, with outside dimensions essentially the same as the inside dimensions of the syringe tip (301) and inside dimensions essentially the same as the outside dimensions of the insertion shaft (203). The deformed shape of the insertion nose (103) makes a lock-and-key seal with the inside dimensions of the syringe tip (301). As the insertion body (200) is inserted over the expansion sleeve (100), the locking flanges (213) on the locking barrel (210) will be inserted over the proximal edge of the conical collar (110). When the two components of the adaptor are fully pressed together, the locking flanges (213) disposed on the inner surface (212) of the locking barrel (210) will engage the projecting flanges (113) disposed on the outer surface of the conical collar (110) to secure the insertion body (200), expansion sleeve (100) and syringe (300) in a locked configuration.

Figure 8:
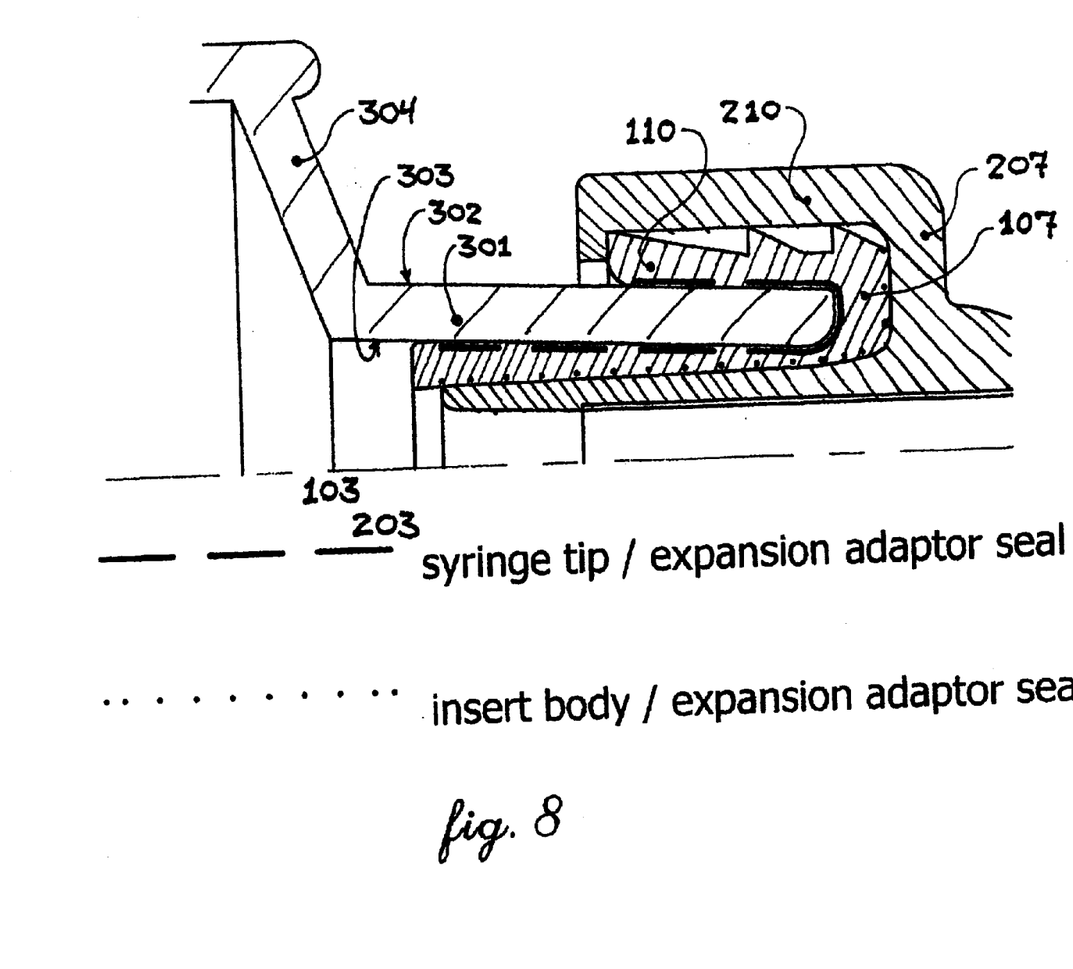
FIG. 8 is an enlarged cross-sectional side view of the sealing mechanisms and material interfaces of the expansion sleeve/insertion body of FIG. 4A when it is fully engaged with the syringe tip.

FIG. 8 depicts two continuous seals formed when the components of the adaptor are interconnected. Specifically, one seal extends from the proximal end of the insertion shaft (203), along its outer surface (204), to the locking flanges (213) disposed on the inner surface (212) of the barrel (210). The other seal extends from the proximal end of the deformed nose (103), along its outer surface (104), proximal end of the conical collar (110), along its inner surface (112). These two continuous seals ensure that the fluid communication between the adaptor and the syringe is uninterrupted and uncompromised during use of the assembly.

Figure 9A:
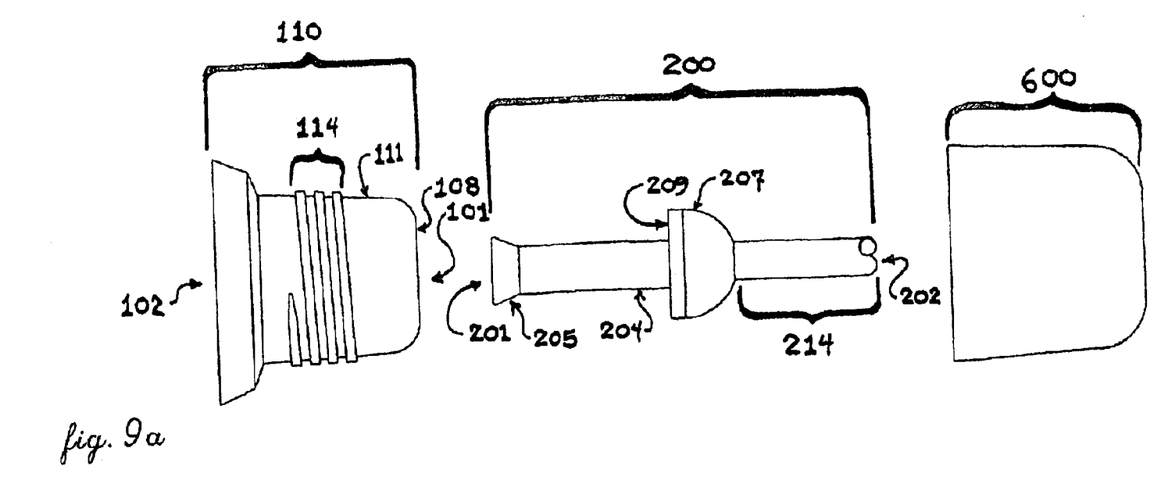
FIG. 9A is an enlarged side view of the components of an alternate embodiment of the syringe adaptor of the present invention, referred to as the screw embodiment.
Figure 9B:
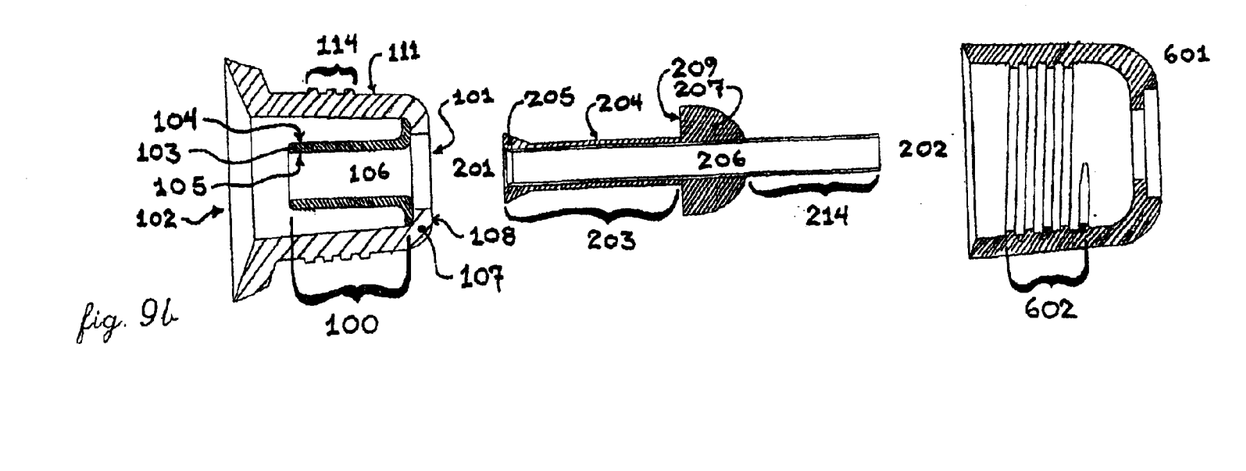
FIG. 9B is an enlarged side cross-sectional view of the components of the screw embodiment of the syringe adaptor.
Figure 10A:
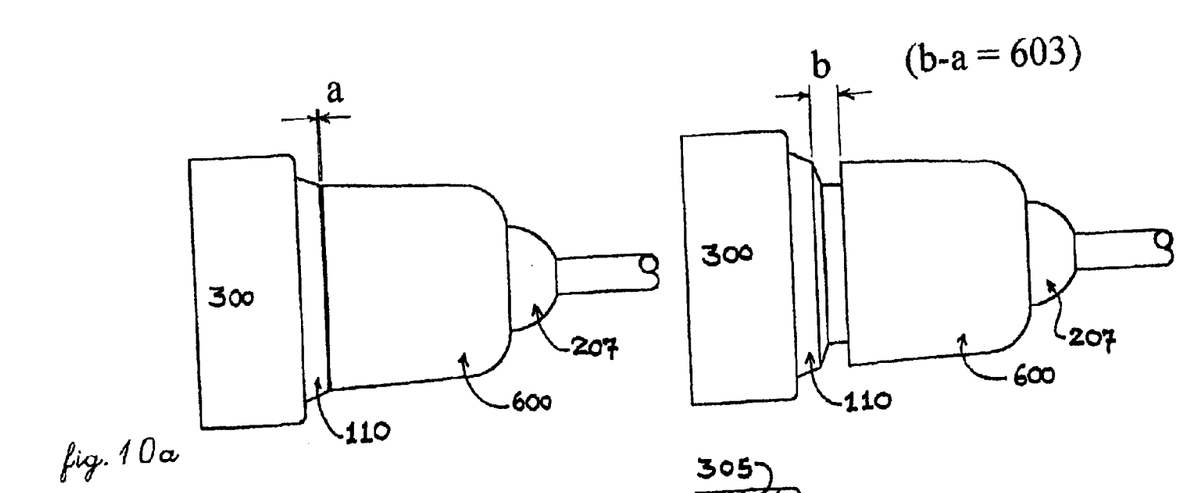
FIG. 10A is an enlarged side view of the screw embodiment of the adaptor assembled and applied to a syringe (left) and engaged to the syringe (right).
Figure 10B:
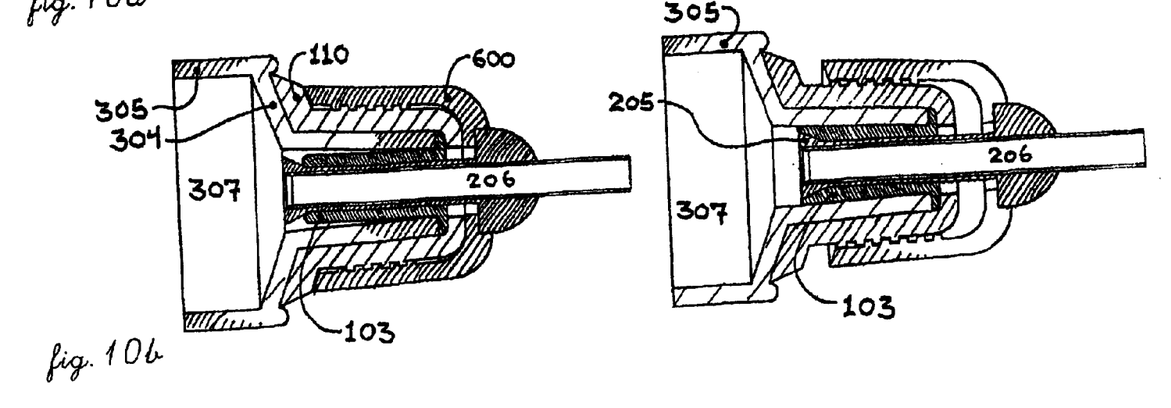
FIG. 10B is an enlarged cross-sectional side view of the screw embodiment of the adaptor assembled and applied to a syringe (left) and engaged to the syringe (right).

In another embodiment, depicted in FIGS. 9 and 10, the syringe adaptor operates via a screw mechanism, herein referred to as the screw embodiment of the internal expansion syringe adaptor.

With reference to FIGS. 9A and 9B, a screw embodiment of the internal expansion syringe adaptor can consist of three parts, an expansion sleeve (100), an insertion body (200), and a screw nut (600). The screw nut (600) is analogous to the insertion body barrel (210) of the embodiment depicted in FIG. 1A in that both operate to hold the expansion sleeve (100) and the insertion body (200) snugly together in a locked configuration and to maintain the compression of the outer surface (104) of the expansion sleeve nose (103) against the inner surface of a syringe tip (e.g., 303). Similar to the previous embodiment, the insertion body (200) is received within the expansion sleeve central lumen (106). In the embodiment depicted, the expansion sleeve collar (110) has screw threads (114) disposed about its periphery that engage with the internal screw threads (602) of the screw nut (600). The screw nut has a bearing surface (601) that slidingly engages with the bearing surface of the insertion body (209). As compared to the previous embodiment, the insertion body of the screw embodiment further comprises a horn flair (205) at the proximal end (201). In operation, the insertion body (200) is received within the lumen of the screw nut (606) in such a way that the bearing surface of the expansion sleeve (108) almost contacts the inside surface of the screw nut (608) and the bearing surface of the screw nut (601) contacts the bearing surface of the insertion body shoulder (209).

With reference to FIGS. 10A and 10B, the screw embodiment of the internal expansion syringe adaptor is operated by rotating the screw nut (600) with respect to the expansion sleeve collar (10), thereby engaging the mating screw threads on the screw nut and expansion sleeve (614 and 114, respectively). This rotation translates into linear displacement (603) of the screw nut (600) with respect to the expansion sleeve (100) and syringe (300). This linear displacement is distal with respect to the syringe. The insertion body (200) is received within the expansion sleeve (100) and the screw nut bearing surface (601) is slidingly engaged with the insertion body shoulder bearing surface (209), the two elements forming an interference fit. Therefore, linear displacement of the screw nut (603) causes identical linear displacement of the insertion body (603). As the expansion sleeve nose (103) is held within the syringe tip lumen (306) by the expansion sleeve annular shoulder (107), the wholesale linear displacement of the insertion body compresses the expansion sleeve nose (103) between the insertion body horn flair (205) and the expansion sleeve annular shoulder (107). The compression of the expansion sleeve nose causes radial expansion of the incompressible material until an interference fit and hermetic seal is made with the syringe tip inner surface (303). This process is best depicted in FIG. 10B, wherein the left-side cross-sectional view illustrates the syringe adaptor inserted into the syringe, and the right-side cross-sectional view illustrates it in the engaged configuration. Note the geometry of the expansion adaptor nose (103) in the inserted and engaged illustrations. FIG. 10A best depicts the linear displacement (603) of the screw nut (600) and insertion body (200) with respect to the expansion sleeve collar (110) and syringe (300).

Disengaging and removing the screw embodiment of the internal expansion syringe adaptor requires reverse-rotation of the screw nut (600) with respect to the expansion sleeve (100), thereby allowing the insertion body (200) to return to its prior state (FIG. 10B left-side). In this configuration, the insertion body horn flair (205) no longer compresses the expansion sleeve nose (103). The expansion sleeve nose will return to its previous geometry which, in turn, allows for the removal of the adaptor (400) from the syringe (300).

The primary difference between the embodiments of FIGS. 1 and 9 is the mechanism used to expand the expansion sleeve. In the embodiment of FIG. 9, the radial expansion of the expansion sleeve nose (103) is caused by displacement of the expansion sleeve nose material due to the insertion of the insertion body shaft (203), whereas in the embodiment of FIG. 1, the radial expansion of the expansion sleeve nose (103) is caused by compressing the expansion sleeve material between the insertion body horn flair (205) and the expansion sleeve annular shoulder (107).

Figures 11A, 11B:
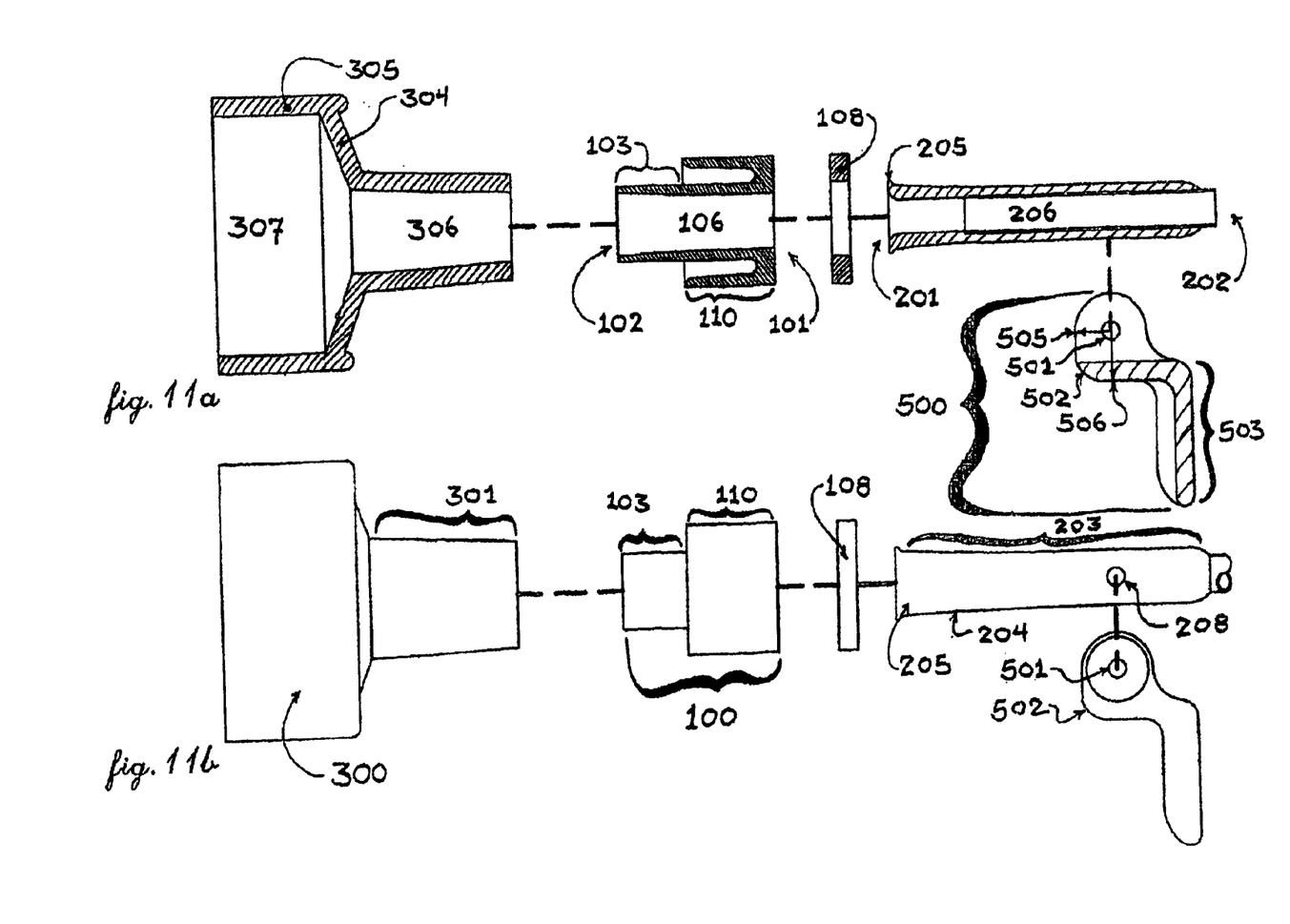
FIG. 11A is an enlarged side view of the components of another embodiment of the syringe adaptor, referred to as the cam-lever embodiment.
FIG. 11B is an enlarged cross-sectional side view of the components of the cam-lever embodiment of the syringe adaptor.
Figure 12A:
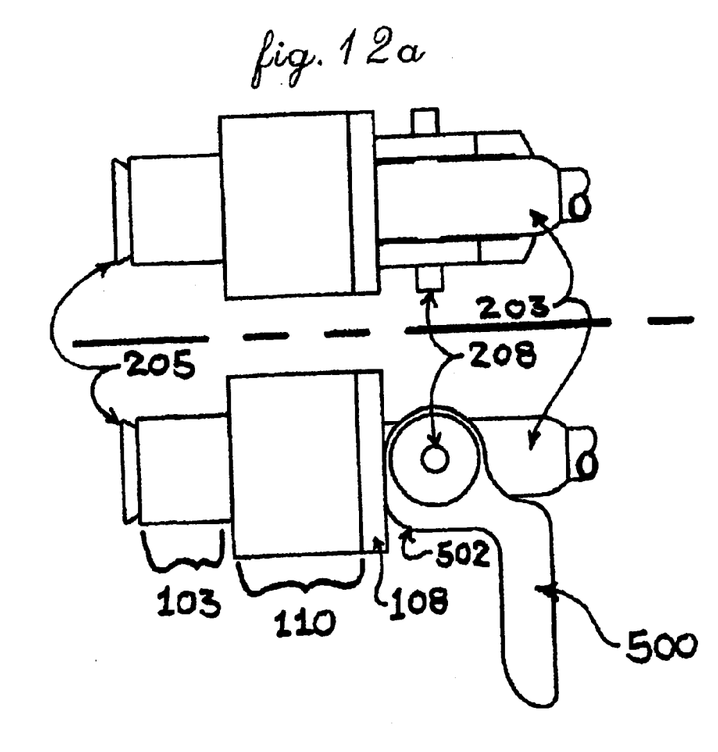
FIG. 12A is an enlarged top and side view of the cam-lever embodiment of FIG. 11A, wherein the components are assembled.
Figure 12B:
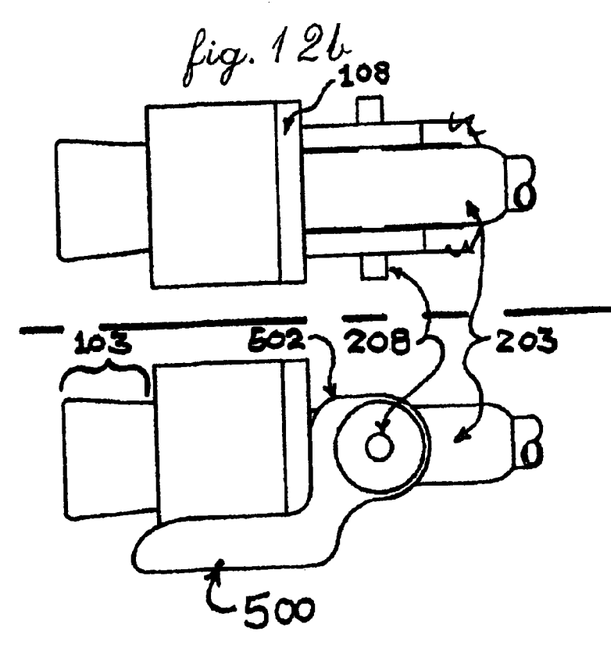
FIG. 12B is an enlarged top and side view of the cam-lever embodiment of FIG. 11A, wherein the components are assembled and engaged to a syringe.
Figure 13:
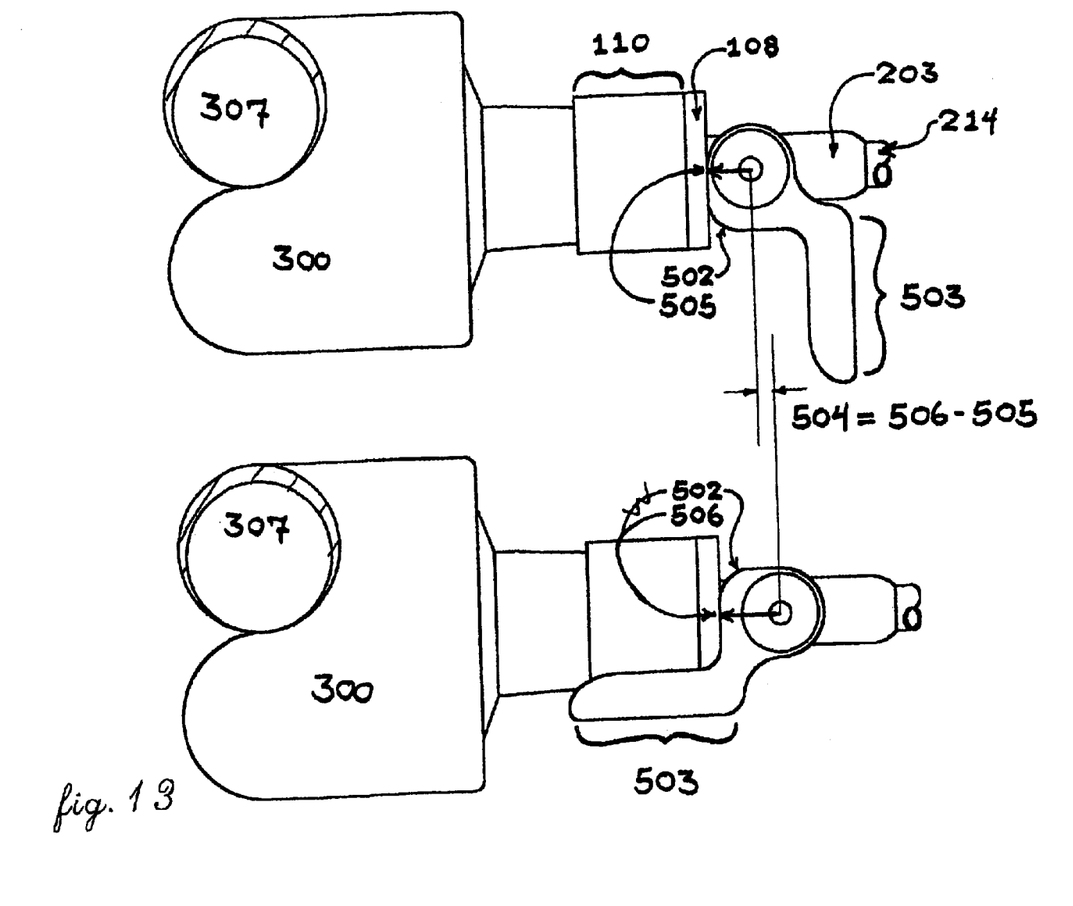
FIG. 13 is an enlarged side view of the cam-lever embodiment of FIG. 11A, assembled and applied to a syringe (top) and engaged to the syringe (bottom).

In yet another embodiment, depicted in FIGS. 11–13, the adaptor operates via a lever mechanism, herein referred to as the lever embodiment of the internal expansion syringe adaptor.

With reference to FIGS. 1A and 1B, the lever embodiment of the internal expansion syringe adaptor consists of three parts: an expansion sleeve (100), an insertion body (200), and a cam lever (500). Similar to the previous embodiments, the insertion body (200) is received within the expansion sleeve central lumen (106). An actuating lever (500) is attached to the insertion body by a mounting pin (208) disposed on the insertion body that pierces mounting pin holes (501) disposed on the lever. Between the expansion sleeve (100) and the actuating lever (500) is a bearing surface (108) that may be integral to the expansion sleeve or provided as a separate piece (depicted as a washer in FIG. 11A). The lever (500) has a cam lobe (502) incorporated into its articulating surface (507). The effective radius from the lever mounting pin hole (501) to the articulating surface (507) is called the resting radius (505) whereas the effective radius from the lever mounting pin hole (501) to the cam-lobe articulating surface (508) is called the activated radius (506).

With reference to FIGS. 12A and 12B, the assembly of the lever embodiment is depicted with the lever (500) in the disengaged position (FIG. 12A) and in the engaged position (12B). In the disengaged position (FIG. 12A), the lever is oriented on the mounting pins (208) such that the articulating surface (507) is in contact with the expansion sleeve bearing surface (108), thus holding the distance between the insertion body mounting pin (208) and the expansion sleeve bearing surface (108) at the resting radius (505). In the engaged position (FIG. 12B), the lever (500) is rotated about the mounting pins (208) such that the articulating surface (508) is in contact with the expansion sleeve bearing surface (108), thus holding the distance between the insertion body mounting pins (208) and the expansion sleeve bearing surface (108) at the activated radius (506). The cam lobe (502) stabilizes the lever in the engaged position. The activated radius (507) is larger than the resting radius (506) and a radial line from the center of the mounting pins (108) to the articulating surface of the cam lobe (502) is larger than either the active or resting radii (506/507). Because the activated radius is larger than the resting radius, engaging the lever causes the insertion body to move distally thereby compressing and radially deforming the expansion adaptor nose (103) between the insert body horn flare (205) and the bearing surface (108). In this manner, the actuating lever (500) is analogous to the insertion body barrel (210) of the embodiment depicted in FIG. 1A and the screw nut (600) of the screw embodiment of FIG. 9A, in that all three elements operate to hold the expansion sleeve (100) and the insertion body (200) snugly together in a locked configuration and to maintain the compression of the outer surface (104) of the expansion sleeve nose (103) against the inner surface of a syringe tip (e.g., 303).

Referring to FIG. 13, the lever embodiment of the internal expansion syringe adaptor is shown inserted into a syringe (top) and engaged to the syringe (bottom).

Removal of the lever embodiment of the internal expansion syringe adaptor requires rotation of the lever (500) to the disengaged position where the distance between the bearing surface (108) and the mounting pins (208) is the resting radius (505).

The inventive adaptor assembly provides numerous advantages over the current art. For example, the deformable expansion sleeve accommodates numerous syringe tips and insertion bodies, regardless of manufacturer or design. Thus, the adaptor of the present invention acts as a universal connector that would accommodate design changes between manufacturers as well as the dimensional instability inherent in the mass production of the component of the assembly. Also, because the tip of the syringe is filled with the deformed hollow nose and insertion shaft, the syringe contents are fully visualized and there is no likelihood for an air space to form.

The continuous fluid-tight fit achieved by continuous deformation of the elastic adaptor can withstand various forms of mechanical loading and thermal changes without interrupting or corrupting the fluids passing through the adaptor mechanism. For example, rotation of the adaptor resulting from torsional loading will not cause detachment of the assembly components or compromise of the fluid-seal. Likewise, mechanical moments, longitudinal, and shear loading will not remove the adaptor from the tip of the syringe or interrupt the fluid-seal.

The deformation locking mechanism allows the adaptor components to be easily separated and cleaned to ensure future sterility of the assembly. Likewise, the nature of the lock-and-key fixation mechanism between syringe and adaptor does not cause any damage, permanent deformations, or adhesive/welding spots to the syringe tip, leaving it in pristine condition. Moreover, the reversibility of the locking and sealing mechanisms allows the adaptor to be applied multiple times, to multiple syringes during the same procedure without any loss of function to the syringe or adaptor mechanism.

As noted above, a number of aspiration and/or irrigation devices may be attached to the distal end of the insertion body. Examples of such devices common in the medical field include, but are not limited to, needles, cannulas, catheters, and other tubing. Industrial devices include caulk gun nozzles and adhesive dispensers.

The intended attached device may be affixed to the distal end of the insertion body by any number of permanent or semi-permanent means. For example, the proximal end of the attached device may be insert molded or welded directly to the distal end of the insertion body. Such an attachment would be sufficient to withstand operating pressures but would release when during the sterilization procedure (e.g., when the assembly is autoclaved). If a more readily interchangeable connection is desired, the distal end of the insertion body may comprise a male Luer tip that coordinates with the female Luer slip on the proximal end of the attached device.

In a preferred embodiment, the attached device is a liposuction cannula. The inventive adaptor is specifically designed to withstand the mechanical manipulations and pressures associated with procedures such as liposuction and lipoplasty.

All references herein are incorporated by reference in their entirety.

While the invention has been described in conjunction with the detailed description thereof, it is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed:

1. An adaptor which connects a syringe, having a syringe tip and syringe tip lumen to an attached device in a mechanically secure and fluid tight manner comprising:

(a) a deformable expansion sleeve, wherein said deformable expansion sleeve comprises a hollow nose, a conical collar coaxially disposed about a periphery of said hollow nose, an annular sleeve shoulder connecting said hollow nose to said conical collar and defining a space between an outer surface of said hollow nose and an inner surface of said conical collar, said space configured, to receive said syringe tip, and a first central lumen running there through; and (b) an insertion body, wherein said insertion body comprises a projecting hollow shaft and a second central lumen running there through;

wherein said hollow nose is deformed by said hollow shaft such that the outer surface of said hollow nose is compressed against an inner surface of said syringe tip lumen forming a fluid tight seal, when the adaptor is connected to the syringe tip further such that said first central lumen and said second central lumen form a continuously sealed passageway.

2. The adaptor of claim 1, wherein an exterior surface of said hollow shaft presses against an inner surface of said hollow nose so as to provide said seal.

3. The adaptor of claim 1, wherein said insertion body further comprises a projection at its proximal end, such that, when said hollow shaft is moved in the distal direction, said hollow nose is compressed between said projection and said annular shoulder so as to provide said seal.

4. The adaptor of claim 1, wherein the distal movement of said hollow shaft is actuated through rotation of a cam lever attached to said insertion body.

5. The adaptor of claim 1, further comprising a locking barrel coaxially disposed about a periphery of said hollow shaft.

6. The adaptor of claim 5, wherein said locking barrel is integral with said insertion body, being disposed about said insertion body shaft and connected thereto by an annular insertion body shoulder.

7. The adaptor of claim 5, wherein said locking barrel comprises a screw nut.

8. The adaptor of claim 5, further comprising a locking element disposed on the outer surface of said conical collar and an engaging element disposed on an inner surface of said locking barrel, wherein said locking element and said engaging element are in direct communication to fixedly connect said sleeve and said insertion body in a fixed, locked relationship.

9. The adaptor of claim 8, wherein the distal movement of said hollow shaft is actuated through the coordination of said locking element with said engaging element.

10. The adaptor of claim 8, wherein said locking element comprises a screw thread and said engaging element comprises a screw track.

11. The adaptor of claim 8, wherein said locking element comprises a ratchet and said engaging element comprises a pawl.

12. The adaptor of claim 8, wherein said locking element comprises a notch and said engaging element comprises a groove.

13. The adaptor of claim 1, wherein said deformable expansion sleeve is formed from an elastomeric material.

14. The adaptor of claim 13, wherein said elastomeric material is selected from the group consisting of cross-linked silicone, low density polyethylene, rubber, wax, fabric, textile, felt, weave, low-modulus metal, hydrogel, swelling material (anhydrous or non-water-absorbing), clay, bingham plastic, caulk, glue and potting material.

15. The adaptor of claim 1, wherein said insertion body is formed from a relatively rigid material.

16. The adaptor of claim 15, wherein said rigid material is selected from the group consisting of metal, engineering plastics, and ceramics.

17. The adaptor of claim 1, wherein said syringe tip, hollow nose, and hollow shaft are concentrically disposed such that said hollow nose has an outside diameter that is smaller than an inside diameter of said syringe tip and an inside diameter that is smaller than an outside diameter of said hollow shaft.

18. The adaptor of claim 5, wherein said conical collar has an outside diameter that is substantially similar to an inside diameter of said locking barrel.

19. The adaptor of claim 6, wherein said sleeve shoulder abuts said insertion body shoulder when said expansion sleeve and said insertion body are fitted together.

20. The adaptor of claim 6, wherein said sleeve should abuts an inner surface of said locking barrel when said expansion sleeve and said insertion body are fitted together.

21. The adaptor of claim 1, wherein said syringe tip, hollow nose and hollow shaft are concentrically disposed such that said hollow shaft has an outside diameter that is smaller than an inside diameter of said syringe tip but larger than an inside diameter of said hollow sleeve nose of said deformable expansion sleeve.

22. The adaptor of claim 5, wherein said locking barrel comprises finger recesses disposed on an outer surface of said locking barrel.

23. A syringe-adaptor assembly comprising:
   (a) the adaptor of claim 1; and
   (b) a syringe comprising an open barrel, a tapered syringe tip, and an annular shoulder joining said barrel to said tip;
   wherein said syringe tip is lockingly engaged between said hollow nose of said deformable expansion sleeve and conical collar, thereby forming a lock-and-key seal.

24. The assembly of claim 23, wherein said insertion body and said deformable expansion sleeve are fitted with coordinating locking elements, such that said insertion body may be fixedly connected and locked to said deformable expansion sleeve.

25. The assembly of claim 23, wherein said insertion body is fitted with an aspiration and/or irrigation device at a distal end of said insertion body.

26. The assembly of claim 25, wherein said aspiration/irrigation device is connected to said body via a semi-permanent insert molding or weld.

27. The assembly of claim 25, wherein said aspiration/irrigation device is a medical device selected from the group consisting of catheters, cannulas and needles.

28. The assembly of claim 25, wherein said aspiration/irrigation device is a liposuction cannula.

* * * * *